United States Patent
Prilutsky

(10) Patent No.: US 11,016,951 B1
(45) Date of Patent: May 25, 2021

(54) MICROBATCH LOADING

(71) Applicant: Allscripts Software, LLC, Raleigh, NC (US)

(72) Inventor: Roman Prilutsky, Beer Sheva (IL)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 244 days.

(21) Appl. No.: 16/199,209

(22) Filed: Nov. 25, 2018

Related U.S. Application Data

(63) Continuation of application No. 14/292,815, filed on May 30, 2014, now Pat. No. 10,140,318.

(60) Provisional application No. 61/841,815, filed on Jul. 1, 2013.

(51) Int. Cl.
  *G06F 16/21* (2019.01)
  *G16H 10/60* (2018.01)
  *G06F 16/23* (2019.01)

(52) U.S. Cl.
  CPC ............ *G06F 16/21* (2019.01); *G06F 16/23* (2019.01); *G16H 10/60* (2018.01)

(58) Field of Classification Search
  CPC ........ G06Q 50/22; G06Q 50/24; G06Q 10/06; G16H 40/20; G16H 10/60; H04L 67/06; G06F 16/21; G06F 16/23
  See application file for complete search history.

(56) References Cited

U.S. PATENT DOCUMENTS

| | | | |
|---|---|---|---|
| 9,131,010 B2* | 9/2015 | Agrawal | H04L 67/06 |
| 2004/0019501 A1* | 1/2004 | White | G16H 40/20 |
| | | | 705/2 |
| 2004/0249250 A1 | 12/2004 | McGee et al. | |
| 2007/0100659 A1 | 5/2007 | Preiss | |
| 2007/0118601 A1 | 5/2007 | Pacheco | |
| 2007/0234369 A1* | 10/2007 | Paramisivam | G06Q 10/06 |
| | | | 719/313 |
| 2010/0191546 A1 | 7/2010 | Kanamarlapudi et al. | |
| 2011/0258000 A1* | 10/2011 | Green | G06Q 50/24 |
| | | | 705/3 |
| 2012/0130730 A1 | 5/2012 | Setlur et al. | |
| 2013/0054678 A1* | 2/2013 | Williams | G06Q 50/22 |
| | | | 709/203 |
| 2014/0278537 A1* | 9/2014 | Antony | G16H 40/20 |
| | | | 705/3 |

OTHER PUBLICATIONS

"Preliminary Amendment for U.S. Appl. No. 14/292,815", filed Aug. 25, 2014, 10 pages.
"Non-Final Office Action for U.S. Appl. No. 14/292,815", dated Feb. 26, 2016, 17 pages.
"Response to the Non-Final Office Action for U.S. Appl. No. 14/292,815", filed Jun. 27, 2016, 4 pages.
"Final Office Action for U.S. Appl. No. 14/292,815", dated Aug. 4, 2016, 20 pages.

(Continued)

*Primary Examiner* — Etienne P Leroux
(74) *Attorney, Agent, or Firm* — Medley, Behrens & Lewis, LLC

(57) ABSTRACT

A method includes receiving structured clinical data in transactional HL7 messages, aggregating the data in a staging area, and merging only the most updated data into a destination database in ordered validated, calculated, and manipulated sets.

15 Claims, 24 Drawing Sheets

(56) References Cited

OTHER PUBLICATIONS

"Notice of Appeal for U.S. Appl. No. 14/292,815", filed Nov. 4, 2016, 2 pages.
"Appeal Brief for U.S. Appl. No. 14/292,815", filed Jan. 2, 2017, 28 pages.
"Appeal Brief for U.S. Appl. No. 14/292,815", filed Apr. 17, 2017, 28 pages.
"Non-Final Office Action for U.S. Appl. No. 14/292,815", dated May 3, 2017, 25 pages.
"Response to the Non-Final Office Action for U.S. Appl. No. 14/292,815", filed Aug. 3, 2017, 15 pages.
"Final Office Action for U.S. Appl. No. 14/292,815", dated Oct. 10, 2017, 27 pages.
"Notice of Appeal for U.S. Appl. No. 14/292,815", filed Jan. 10, 2018, 2 pages.
"Appeal Brief for U.S. Appl. No. 14/292,815", filed May 10, 2018, 34 pages.
"Notice of Allowance and Fees Due for U.S. Appl. No. 14/292,815", dated Jul. 12, 2018, 14 pages.

* cited by examiner

```
SELECT Stg_PR.PatientRecordID, Stg_PR.LoadId, CDR_PR.PatientRecordID as CDR_PID,
       CDR_PR.IsVirtual as  CDR_IsVirtual,Stg_PR.LoadPolicy,
       ROW_NUMBER() OVER(PARTITION BY Stg_PR.PrimaryRoot, Stg_PR.PrimaryExtension ORDER BY Stg_PR.LoadID DESC)
    AS RowNum
FROM PatientAdministration.PatientRecord AS Stg_PR LEFT OUTER JOIN
  POC_dbmVCDRData.PatientAdministration.PatientRecord AS CDR_PR ON
  Stg_PR.PrimaryRoot = CDR_PR.PrimaryRoot AND Stg_PR.PrimaryExtension = CDR_PR.PrimaryExtension
```

```
DECLARE @NamIdsTable TABLE
(CDRPatientNameID bigint not null, StagePatientNameID bigint not null, LoadID bigint not null, PatientRecordID bigint not null);

declare @DeletedIds table (Id bigint);

DELETE PN
OUTPUT deleted.PatientNameID INTO @DeletedIds
FROM [POC_dbmVCDRData].[PatientAdministration].[PatientName] PN INNER JOIN
    [PatientAdministration].[PatientRecordTier2] PR ON PN.PatientRecordID = PR.[CDRPatientRecordID]
WHERE PR.CDCFlag IN ('U','R');

DELETE PNP
FROM [POC_dbmVCDRData].[PatientAdministration].[PatientNamePart] PNP INNER JOIN
    @DeletedIds IDS ON IDS.Id = PNP.PatientNameID;

MERGE [POC_dbmVCDRData].[PatientAdministration].[PatientName] AS target
USING (SELECT PN.[NameVzeID], PR.[CDRPatientRecordID], PR.LoadID, PN.[PatientNameID]
    FROM [PatientAdministration].[PatientName] PN INNER JOIN
        [PatientAdministration].PatientRecordTier2 PR ON PN.PatientRecordID = PR.[CDRPatientRecordID] AND PR.CDCFlag = 'U')
    AS source
ON (source.[CDRPatientRecordID] = target.PatientRecordID)
WHEN NOT MATCHED BY TARGET THEN
    INSERT VALUES (source.[NameVzeID], source.[CDRPatientRecordID], source.LoadID)
OUTPUT inserted.[PatientNameID], source.[PatientNameID], inserted.ControlAcID, inserted.PatientRecordID INTO @NamIdsTable;

INSERT INTO [POC_dbmVCDRData].[PatientAdministration].[PatientNamePart]
SELECT Value, PartTypeID, QualifierID, CDRPatientNameID, IDS.LoadID
FROM [PatientAdministration].[PatientNamePart] PNP INNER JOIN @NamIdsTable IDS ON
    PNP.LoadID=IDS.LoadID AND PNP.PatientNameID=IDS.StagePatientNameID
```

```
;MERGE [POC_dbmVCDRData].[PatientAdministration].[PatientConfidentiality] as target
USING (SELECT PC.*, PR.CDCFlag, PR.CDRPatientRecordID FROM [PatientAdministration].[PatientConfidentiality]
        AS PC INNER JOIN [PatientAdministration].[PatientRecordTier2] AS PR ON
        PC.LoadID = PR.LoadID AND PO.PatientRecordID = PR.PatientRecordID) AS source
ON (target.PatientRecordID = source.[CDRPatientRecordID] AND target.ConfidentialityCodeID = source.ConfidentialityCodeID)
WHEN NOT MATCHED AND source.CDCFlag='U' THEN
    INSERT VALUES (source.[ConfidentialityCodeID], source.[CDRPatientRecordID], source.[LoadId])
WHEN MATCHED AND source.CDCFlag='R' THEN
    DELETE;

DELETE PRC
FROM [POC_dbmVCDRData].[PatientAdministration].[PatientConfidentiality] PRC
INNER JOIN [PatientAdministration].[PatientRecordTier2] AS PR ON PRC.PatientRecordID = PR.[CDRPatientRecordID]
LEFT OUTER JOIN [PatientAdministration].[PatientConfidentiality] SPRC ON PRC.PatientRecordID = SPRC.PatientRecordID
AND PRC.ConfidentialityCodeID = SPRC.ConfidentialityCodeID AND SPRC.PatientRecordID=PR.[CDRPatientRecordID]
AND SPRC.LoadID=PR.LoadID
WHERE SPRC.PatientConfidentialityID is NULL AND PR.CDCFlag <> 'R';
```

*FIG. 21*

MICROBATCH LOADING

RELATED APPLICATIONS

This application is a continuation of U.S. patent application Ser. No. 14/292,815, filed on May 30, 2014, and entitled "MICROBATCH LOADING", which claims priority to U.S. Provisional Patent Application No. 61/841,815, filed Jul. 1, 2013. The afore-mentioned applications are incorporated in their entireties herein by reference.

The present application also hereby incorporates herein by reference the entire disclosure of Exhibits A, B, and C attached hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to systems and methodologies for loading data.

Some systems include a large data flow that needs to be loaded into a data repository, such as a database. As the data flow increases, e.g. as the amount of data that needs to be loaded per second grows, it can become increasingly difficult to keep up.

Needs exist for improvement in loading data. These, and other needs, are addressed by one or more aspects of the present invention.

SUMMARY OF THE INVENTION

The present invention includes many aspects and features. Moreover, while many aspects and features relate to, and are described in, the context of health care, the present invention is not limited to use only in this context, as will become apparent from the following summaries and detailed descriptions of aspects, features, and one or more embodiments of the present invention.

Accordingly, one aspect of the present invention relates to a system in which structured clinical data received in transactional HL7 messages is aggregated in a staging area, and only the most updated data is merged into a destination database in ordered, validated, calculated, and manipulated sets.

Another aspect relates to a method comprising: electronically receiving, over a network, a plurality of HL7 transactional messages containing patient data for a plurality of patients; electronically sorting, at one or more electronic devices, the plurality of HL7 transactional messages into a plurality of patient queues, each patient queue representing a queue for HL7 transactional messages containing data for a respective particular patient of the plurality of patients; electronically validating, at an electronic device, a first plurality of HL7 transactional messages for a first particular patient by evaluating the HL7 transactional messages against a plurality of rules; electronically aggregating, at an electronic device, the first plurality of HL7 transactional messages for the first particular patient; electronically merging, utilizing one or more processors, information corresponding to the first aggregated HL7 transactional messages for the first particular patient into a centralized data repository, one or more servers comprising the centralized data repository; electronically validating, at an electronic device, a second plurality of HL7 transactional messages for the first particular patient by evaluating the HL7 transactional messages against a plurality of rules; electronically aggregating, at an electronic device, the second plurality of HL7 transactional messages for the first particular patient; electronically merging, utilizing one or more processors, information corresponding to the second aggregated HL7 transactional messages for the first particular patient into the centralized data repository; electronically validating, at an electronic device, a third plurality of HL7 transactional messages for a second particular patient by evaluating the HL7 transactional messages against a plurality of rules; electronically aggregating, at an electronic device, the third plurality of HL7 transactional messages for the second particular patient; electronically merging, utilizing one or more processors, information corresponding to the third aggregated HL7 transactional messages for the second particular patient into the centralized data repository; attempting to electronically validate, at an electronic device, a fourth plurality of HL7 transactional messages for a third particular patient by evaluating the HL7 transactional messages against a plurality of rules; and determining, based on evaluation of the fourth plurality of HL7 transactional messages against a plurality of rules, that an error occurred when attempting to validate the fourth plurality of HL7 transactional messages.

In a feature of this aspect, the method further includes accessing, by an electronic device, data from the centralized data repository that was merged into the centralized data repository based on information corresponding to the first aggregated HL7 transactional messages for the first particular patient.

In a feature of this aspect, the method further includes displaying, via an electronic display of an electronic device, data from the centralized data repository that was merged into the centralized data repository based on information corresponding to the first aggregated HL7 transactional messages for the first particular patient.

In a feature of this aspect, electronically receiving, over a network, a plurality of HL7 transactional messages containing patient data for a plurality of patients comprises electronically receiving, over a network at a server, a plurality of HL7 transactional messages.

In a feature of this aspect, the number of messages in the first plurality of HL7 transactional messages for the first particular patient is user configurable.

In a feature of this aspect, the method further includes receiving, at an electronic device, input from a user via one or more input devices corresponding to an indication of a number of transactional messages to include in an aggregated "bulk".

In a feature of this aspect, electronically validating, at an electronic device, a first plurality of HL7 transactional messages for a first particular patient by evaluating the HL7 transactional messages against a plurality of rules comprises evaluating the HL7 transactional messages against a plurality of user-customizable rules.

In a feature of this aspect, the method further includes receiving, at an electronic device, input from a user via one or more input devices corresponding to an indication of a number of rule to utilize in evaluating HL7 transactional messages.

In a feature of this aspect, electronically aggregating, at an electronic device, the first plurality of HL7 transactional messages for the first particular patient comprises determining a plurality of CDC operations.

In a feature of this aspect, electronically aggregating, at an electronic device, the first plurality of HL7 transactional messages for the first particular patient comprises determining a plurality of CDC operations, and electronically merging, utilizing one or more processors, information corresponding to the first aggregated HL7 transactional messages for the first particular patient into a centralized data repository comprises utilizing the determined CDC operations.

Another aspect relates to a method comprising electronically receiving, over a network, a plurality of transactional messages containing patient data for a plurality of patients; electronically sorting, at one or more electronic devices, the plurality of transactional messages into a plurality of patient queues, each patient queue representing a queue for transactional messages containing data for a respective particular patient of the plurality of patients; electronically validating, at an electronic device, a first plurality of transactional messages for a first particular patient by evaluating the transactional messages against a plurality of rules; electronically aggregating, at an electronic device, the first plurality of transactional messages for the first particular patient; electronically merging, utilizing one or more processors, information corresponding to the first aggregated transactional messages for the first particular patient into a centralized data repository, one or more servers comprising the centralized data repository; electronically validating, at an electronic device, a second plurality of transactional messages for the first particular patient by evaluating the transactional messages against a plurality of rules; electronically aggregating, at an electronic device, the second plurality of transactional messages for the first particular patient; electronically merging, utilizing one or more processors, information corresponding to the second aggregated transactional messages for the first particular patient into the centralized data repository; electronically validating, at an electronic device, a third plurality of transactional messages for a second particular patient by evaluating the transactional messages against a plurality of rules; electronically aggregating, at an electronic device, the third plurality of transactional messages for the second particular patient; electronically merging, utilizing one or more processors, information corresponding to the third aggregated transactional messages for the second particular patient into the centralized data repository; attempting to electronically validate, at an electronic device, a fourth plurality of transactional messages for a third particular patient by evaluating the transactional messages against a plurality of rules; and determining, based on evaluation of the fourth plurality of transactional messages against a plurality of rules, that an error occurred when attempting to validate the fourth plurality of transactional messages.

Another aspect relates to computer readable media containing computer executable instructions for performing a method comprising electronically receiving, over a network, a plurality of transactional messages containing patient data for a plurality of patients; electronically sorting, at one or more electronic devices, the plurality of transactional messages into a plurality of patient queues, each patient queue representing a queue for transactional messages containing data for a respective particular patient of the plurality of patients; electronically validating, at an electronic device, a first plurality of transactional messages for a first particular patient by evaluating the transactional messages against a plurality of rules; electronically aggregating, at an electronic device, the first plurality of transactional messages for the first particular patient; electronically merging, utilizing one or more processors, information corresponding to the first aggregated transactional messages for the first particular patient into a centralized data repository, one or more servers comprising the centralized data repository; electronically validating, at an electronic device, a second plurality of transactional messages for the first particular patient by evaluating the transactional messages against a plurality of rules; electronically aggregating, at an electronic device, the second plurality of transactional messages for the first particular patient; electronically merging, utilizing one or more processors, information corresponding to the second aggregated transactional messages for the first particular patient into the centralized data repository; electronically validating, at an electronic device, a third plurality of transactional messages for a second particular patient by evaluating the transactional messages against a plurality of rules; electronically aggregating, at an electronic device, the third plurality of transactional messages for the second particular patient; electronically merging, utilizing one or more processors, information corresponding to the third aggregated transactional messages for the second particular patient into the centralized data repository; attempting to electronically validate, at an electronic device, a fourth plurality of transactional messages for a third particular patient by evaluating the transactional messages against a plurality of rules; and determining, based on evaluation of the fourth plurality of transactional messages against a plurality of rules, that an error occurred when attempting to validate the fourth plurality of transactional messages.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

Figure 18B:
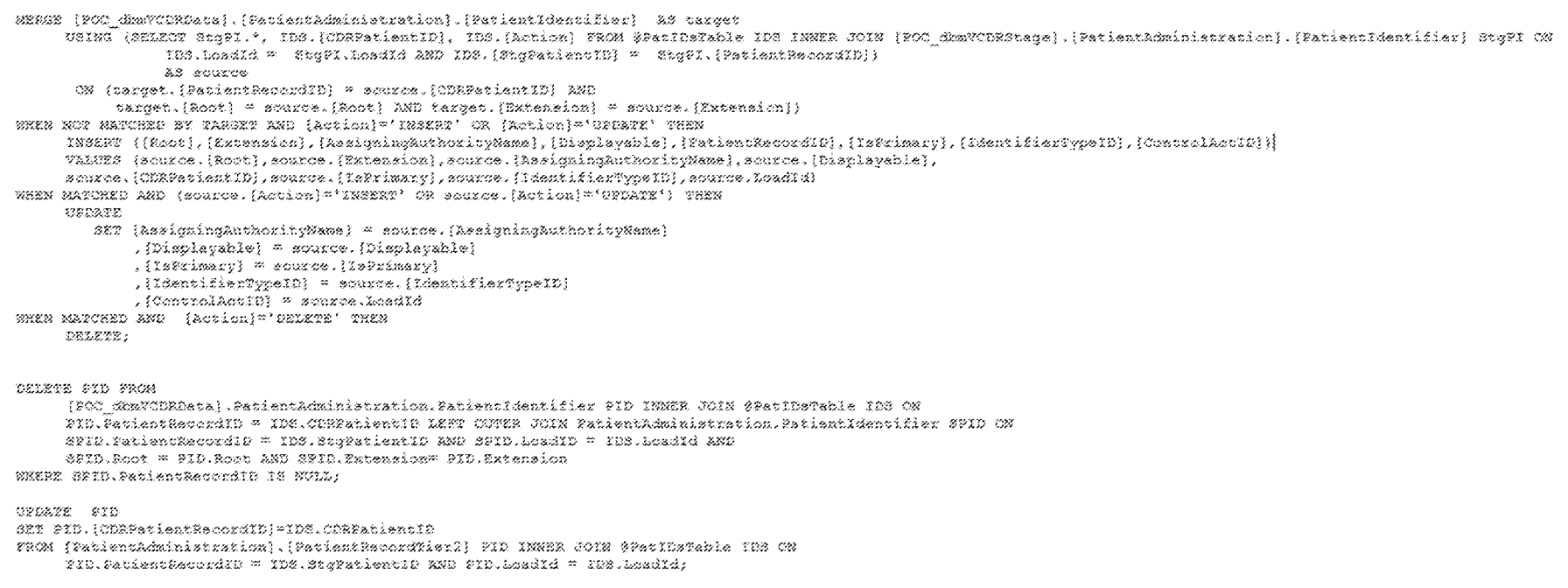

FIGS. 17-21 illustrate exemplary SQL code for processes in accordance with one or more preferred implementations.

DETAILED DESCRIPTION

Figure 1:
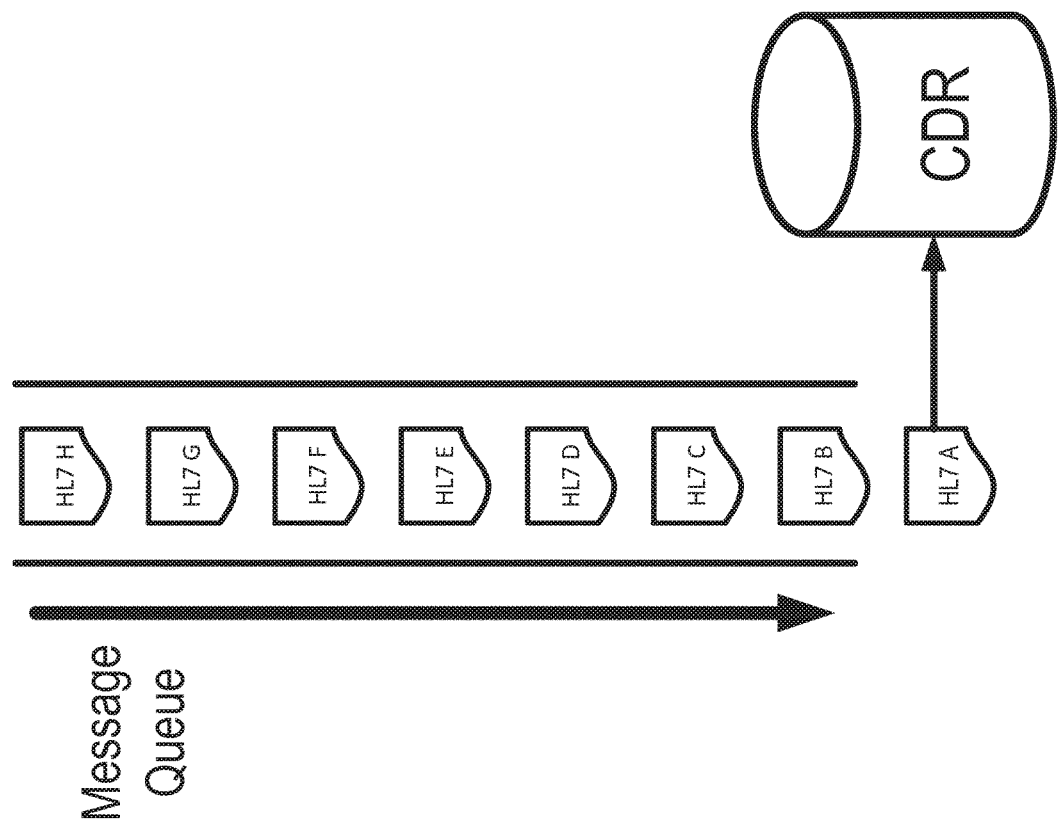
FIGS. 1-2 illustrate an exemplary system in which incoming HL7 messages in a message queue are loaded into a centralized data repository (CDR)

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein-as understood by the Ordinary Artisan based on the contextual use of such term-differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a plcmc basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

An implementation in accordance with one or more preferred embodiments relates to a system in which structured clinical data is communicated in transactional HL7 messages, and received clinical data is loaded into a relational database.

In some such systems, messages are received very frequently (e.g., 100 messages/second), and, further each message might include more than an incremental or transactional change. For example, a message might include other patient/discharge data, and may even include a snapshot of all patient/discharge data for a particular patient. In one or more preferred implementations, clinical data is aggregated in a staging area, and only the most updated data is merged into a destination database in ordered, validated, calculated, and manipulated sets. This preferably reduces processing of reoccurring data, validations, CRUD's, locks, etc.

Figure 2:
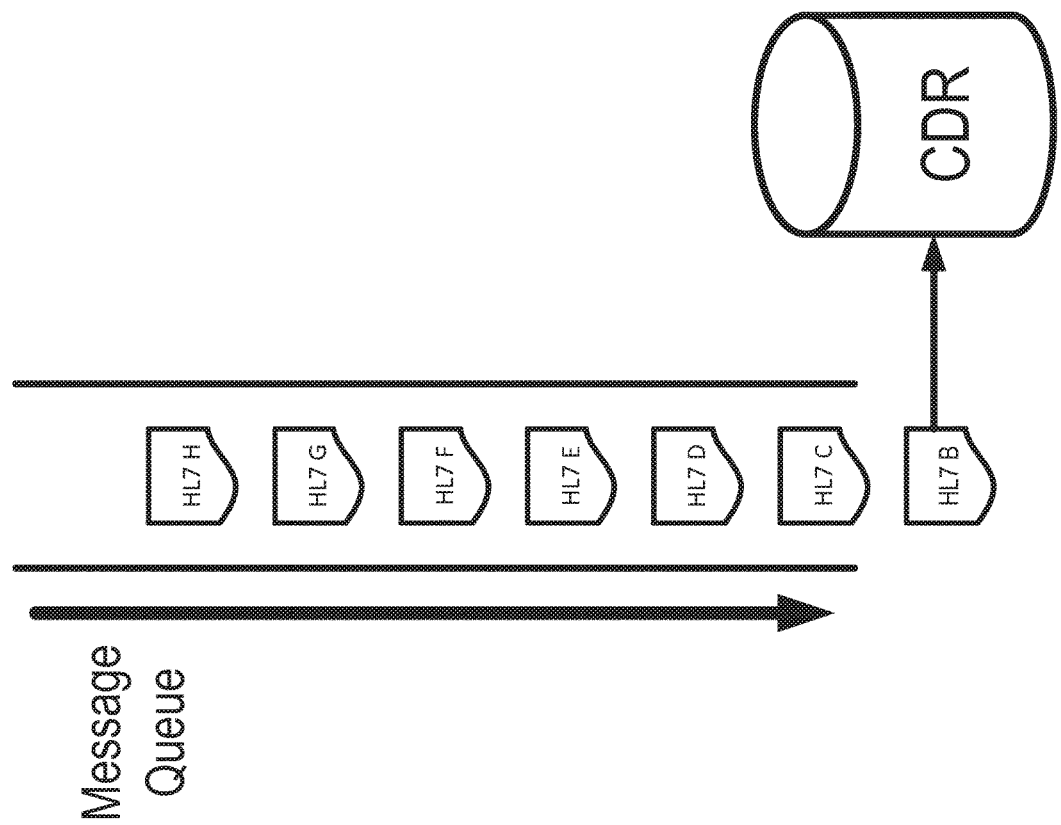

FIG. 1 illustrates an exemplary system in which incoming HL7 messages in a message queue are loaded into a centralized data repository (CDR). As illustrated in FIGS. 1 and 2, the HL7 messages are loaded serially one at a time into the CDR.

Figure 3:
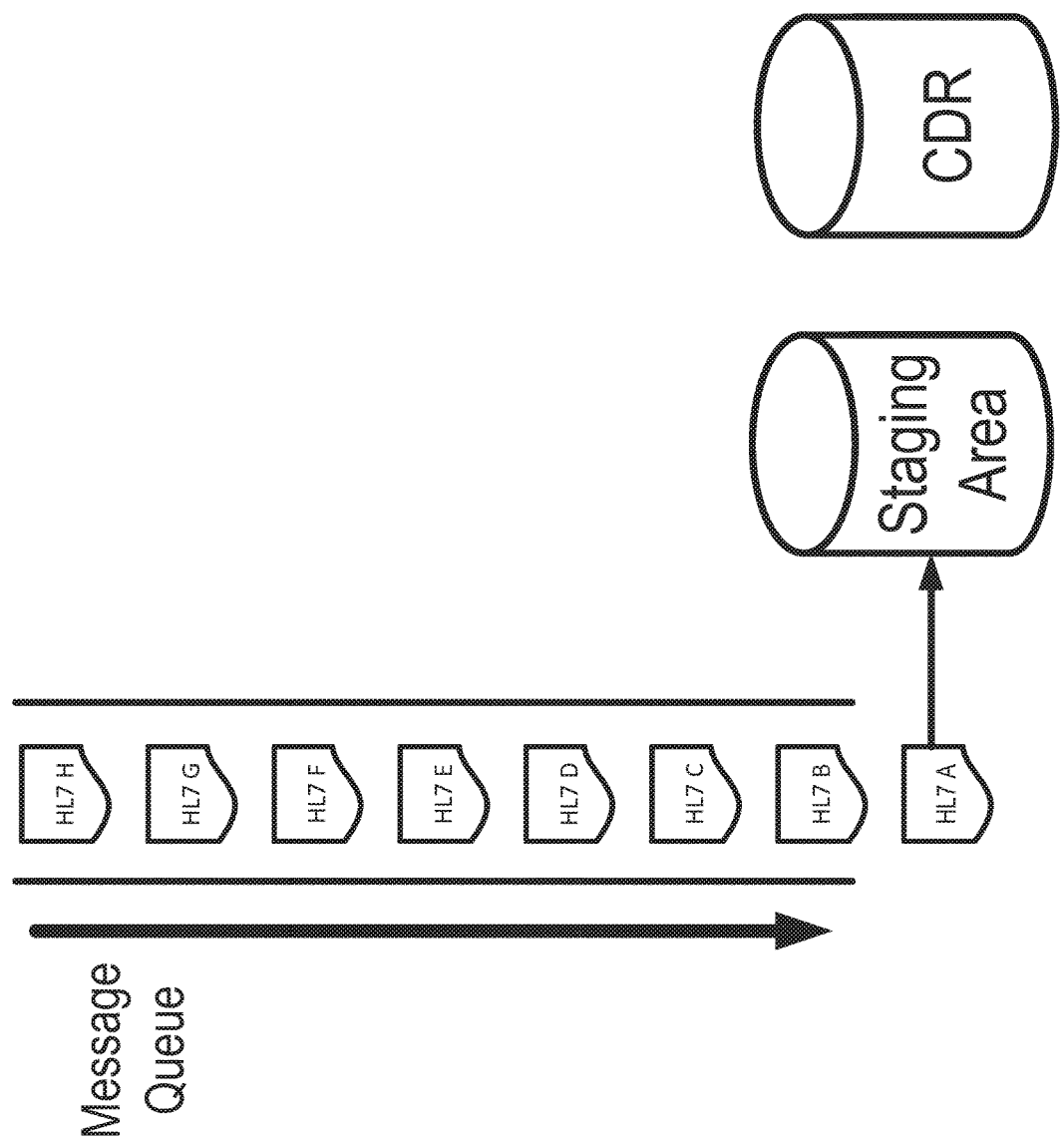
FIGS. 3-6 illustrate an exemplary system in which messages are aggregated in a staging area.
Figure 4:
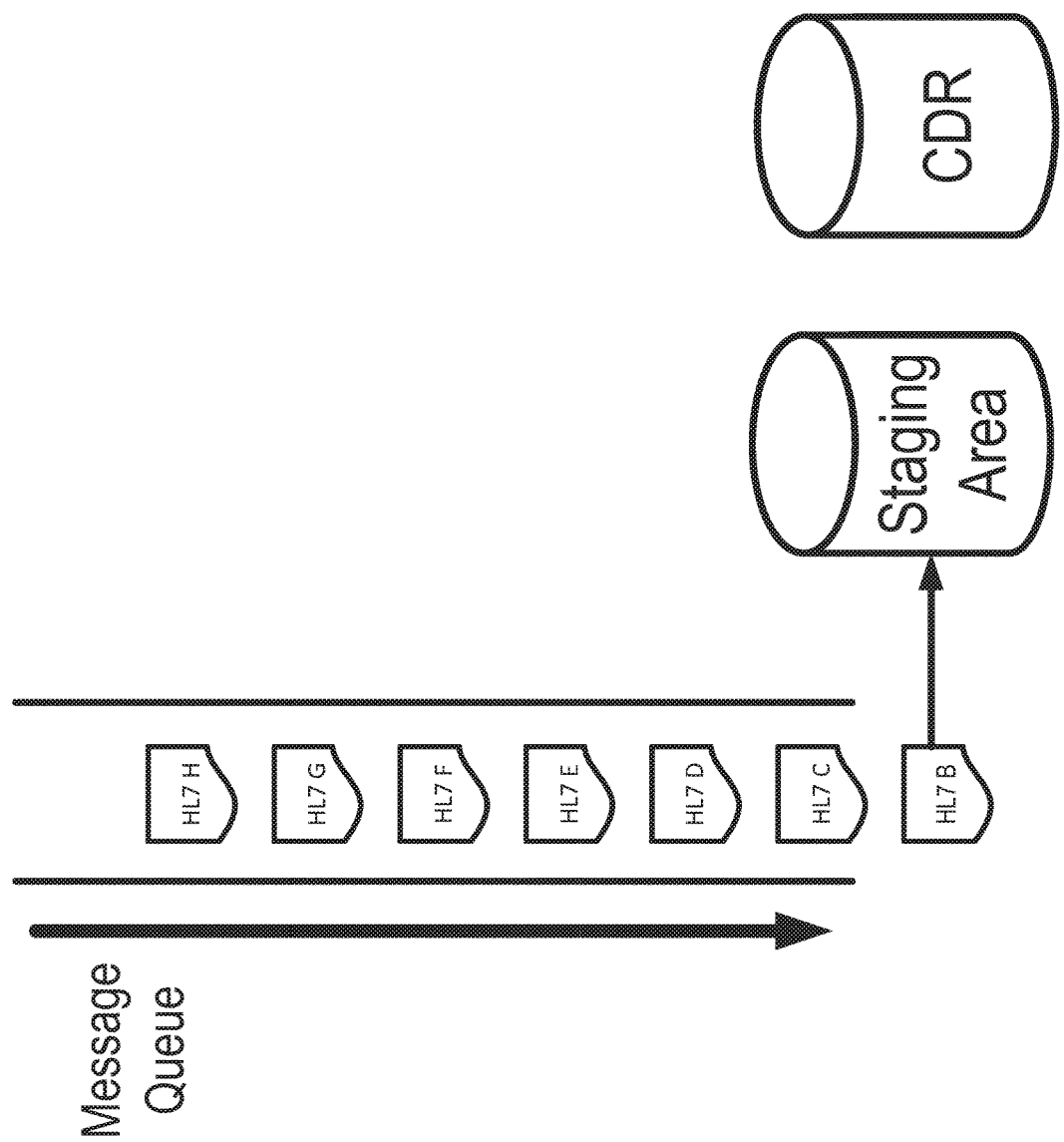
Figure 5:
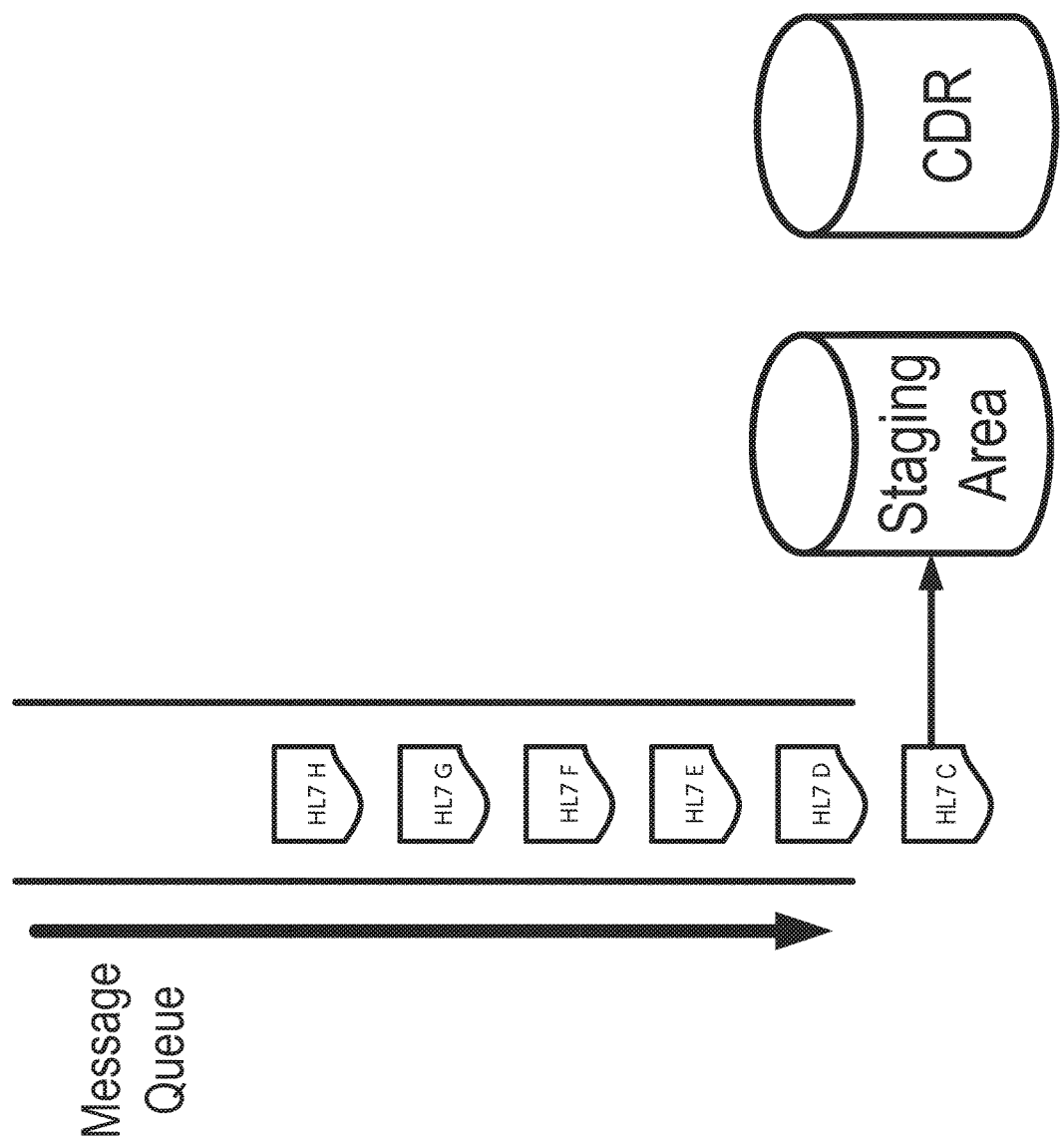
Figure 6:
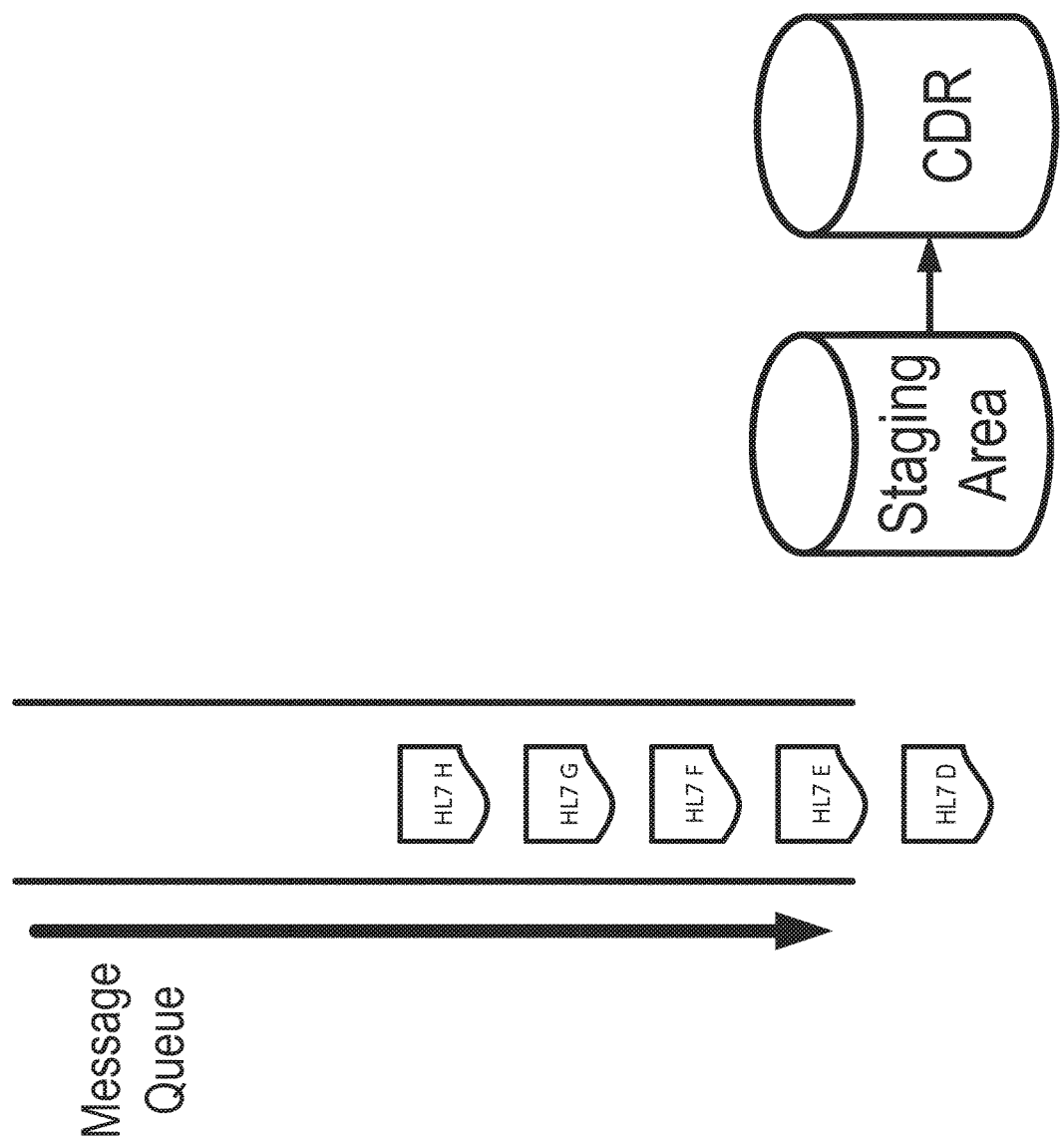
Figure 7:
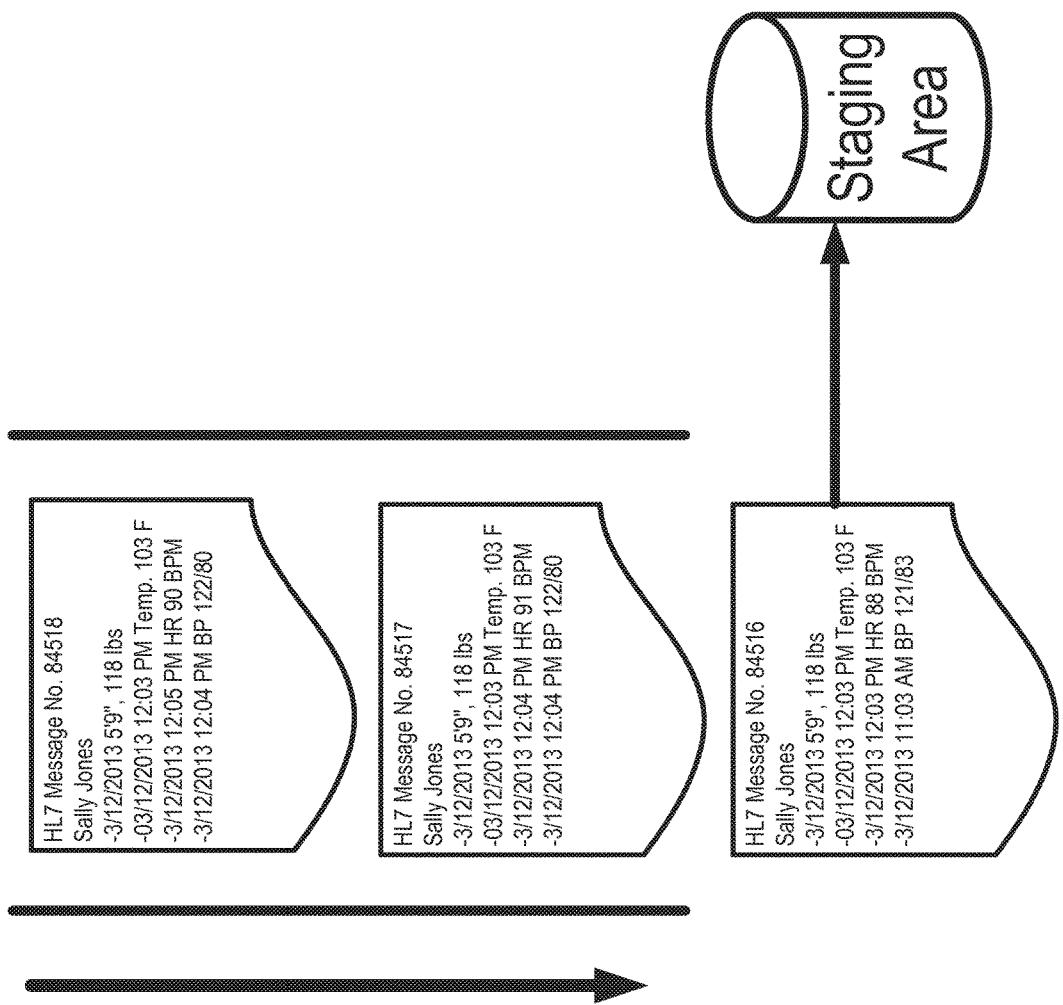
FIGS. 7-10 schematically illustrate aggregation of data from multiple messages at a staging area prior to merging into a CDR.
Figure 8:
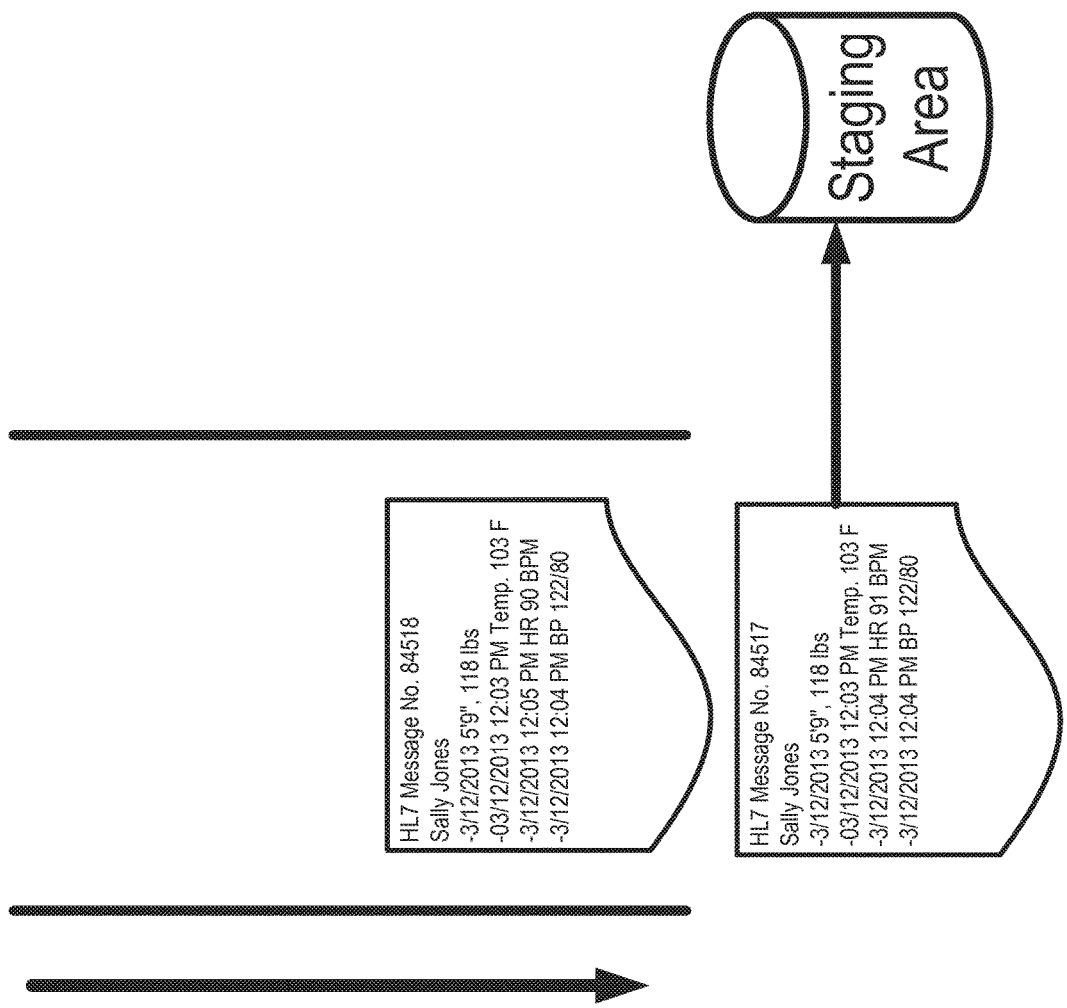
Figure 9:
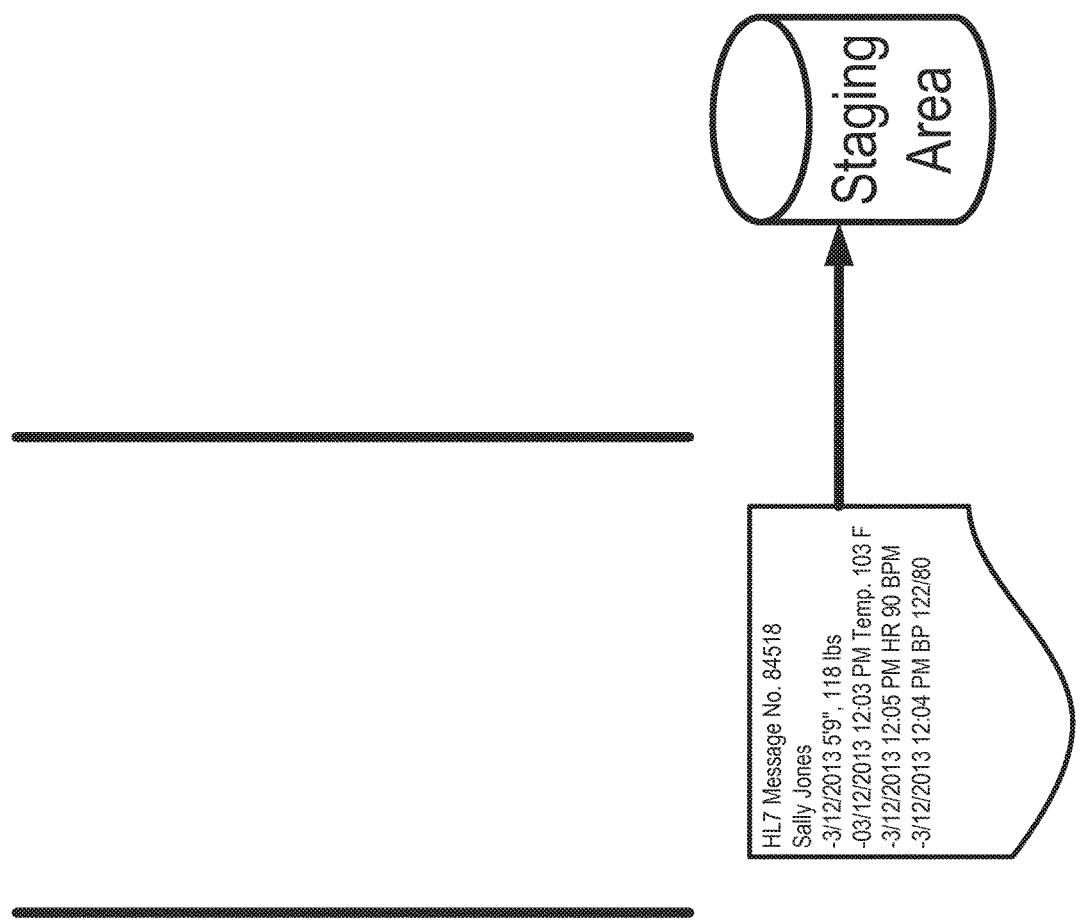
Figure 10:
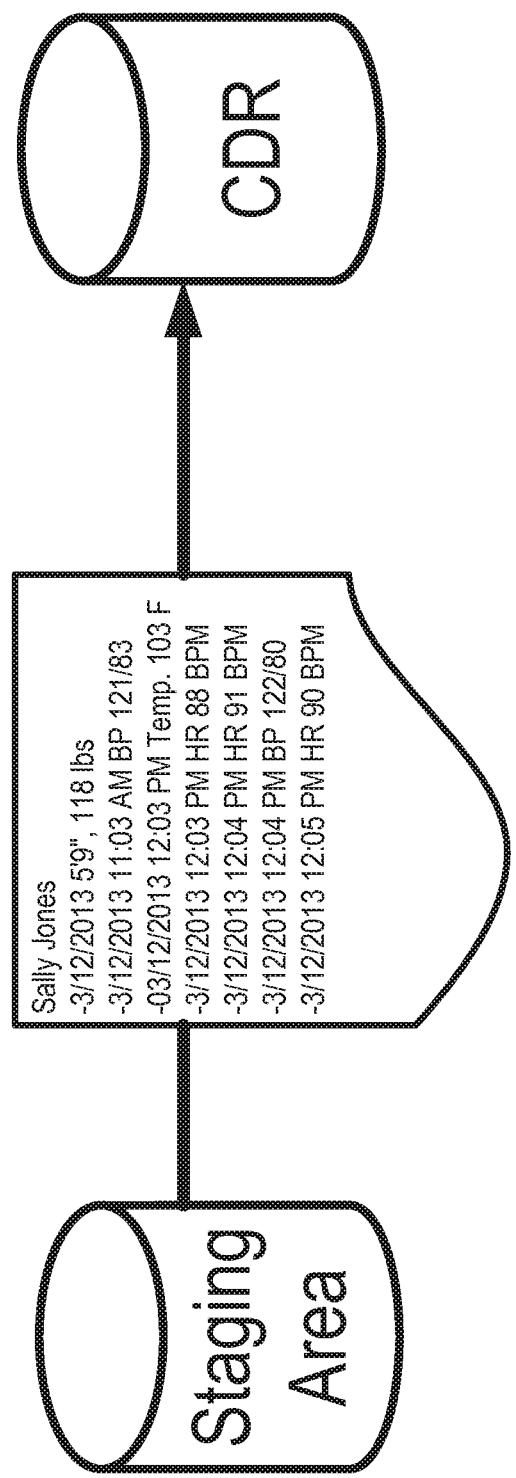

In one or more preferred implementations, rather than being loaded directly into the CDR, messages are aggregated at a staging area, as illustrated in FIGS. 3-5. The messages are preferably aggregated at the staging area such that the data from the messages can then be passed on to the CDR in a more succinct fashion, e.g. in a single transaction or message, as illustrated in FIG. 6.

FIGS. 7-10 schematically illustrate aggregation of data from multiple messages at a staging area prior to merging into a CDR. As illustrated, repetitive data from the messages is not reproduced multiple times and need not be merged into the CDR multiple times, as it potentially would be if each of the messages was loaded sequentially into the CDR. In one or more preferred implementations, this process can be characterized as loading/merging aggregated batches of messages into a destination database, rather than sequentially loading these messages one at time. Although these batches may be of any size, in one or more preferred implementations they are not too large, and can be characterized as microbatches, and the process can be characterized as microbatch loading.

Figure 11:
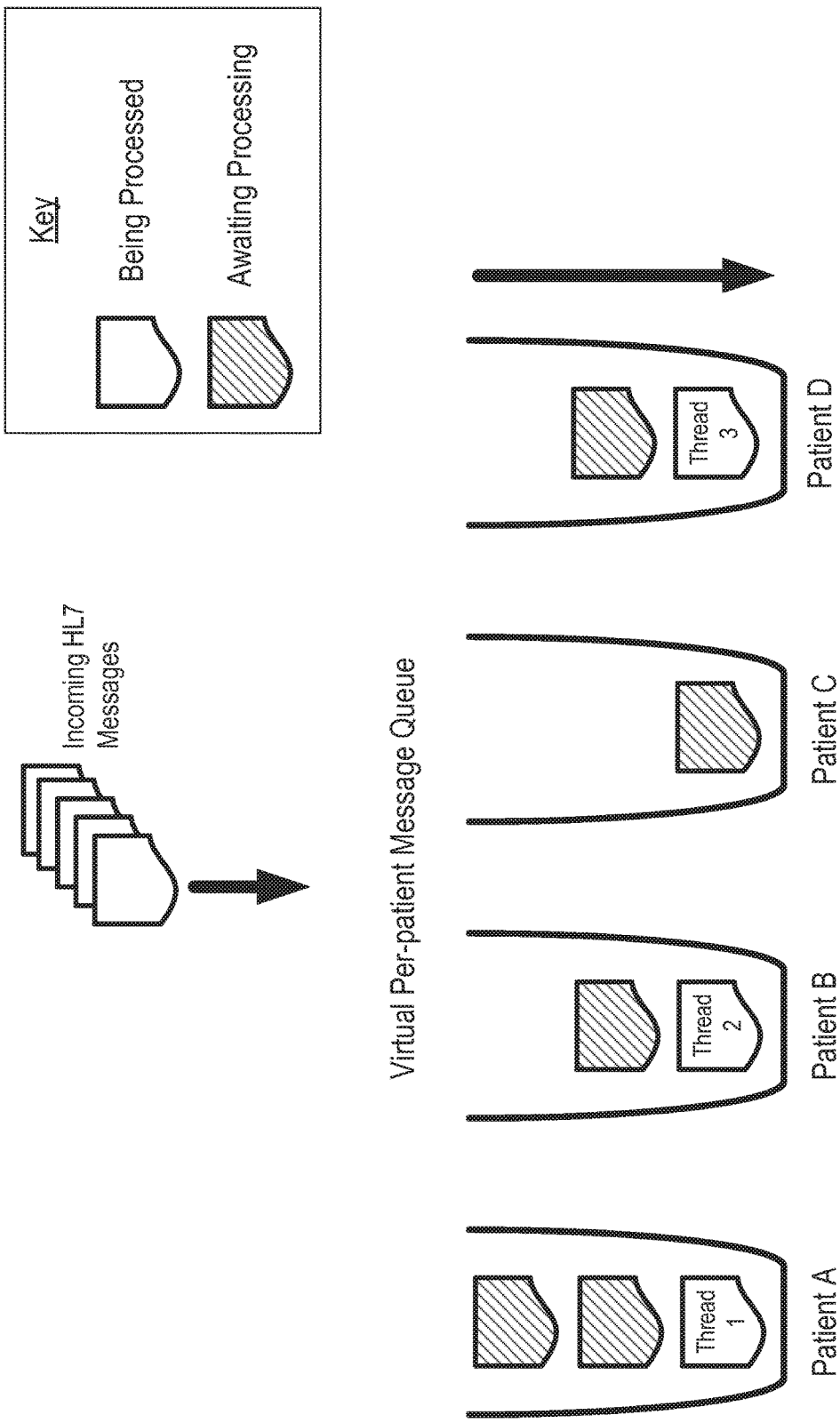
FIG. 11 illustrates use of patient message queues.

In one or more preferred implementations, messages associated with various patients are sorted and each placed into a message queue for the patient they are associated with, as illustrated in FIG. 11. The system is configured for multi-threaded processing, as illustrated. Notably, however, messages in a particular patient queue are processed serially, and thus only a single message in each queue is processed at one time, as illustrated via shading denoting whether a message is being processed.

Figure 12:
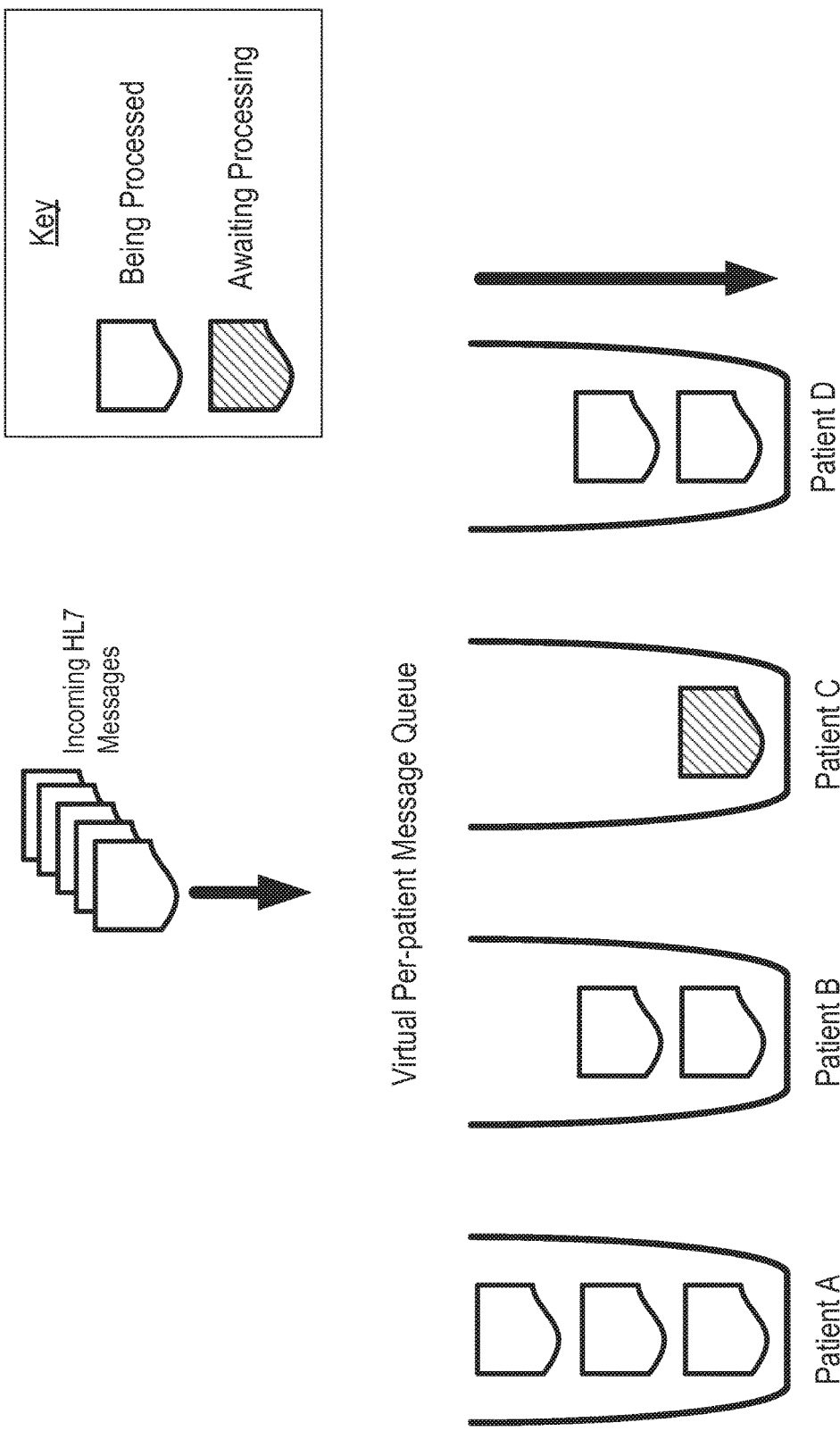
FIG. 12 illustrates the processing of multiple messages in a single patient message queue.

In one or more preferred implementations, multiple received HL7 messages associated with a patient are aggregated and then merged to a destination database. In effect, this allows multiple messages for a single patient to be processed at once, as illustrated in FIG. 12.

In one or more preferred implementations, optimization allows for the processing of a chunk of a number of messages, e.g. n messages, in one bulk. In one or more preferred implementations, this allows several messages to be aggregated/merged before commit. In one or more preferred implementations, RDBMS set operations are leveraged.

Figure 13:
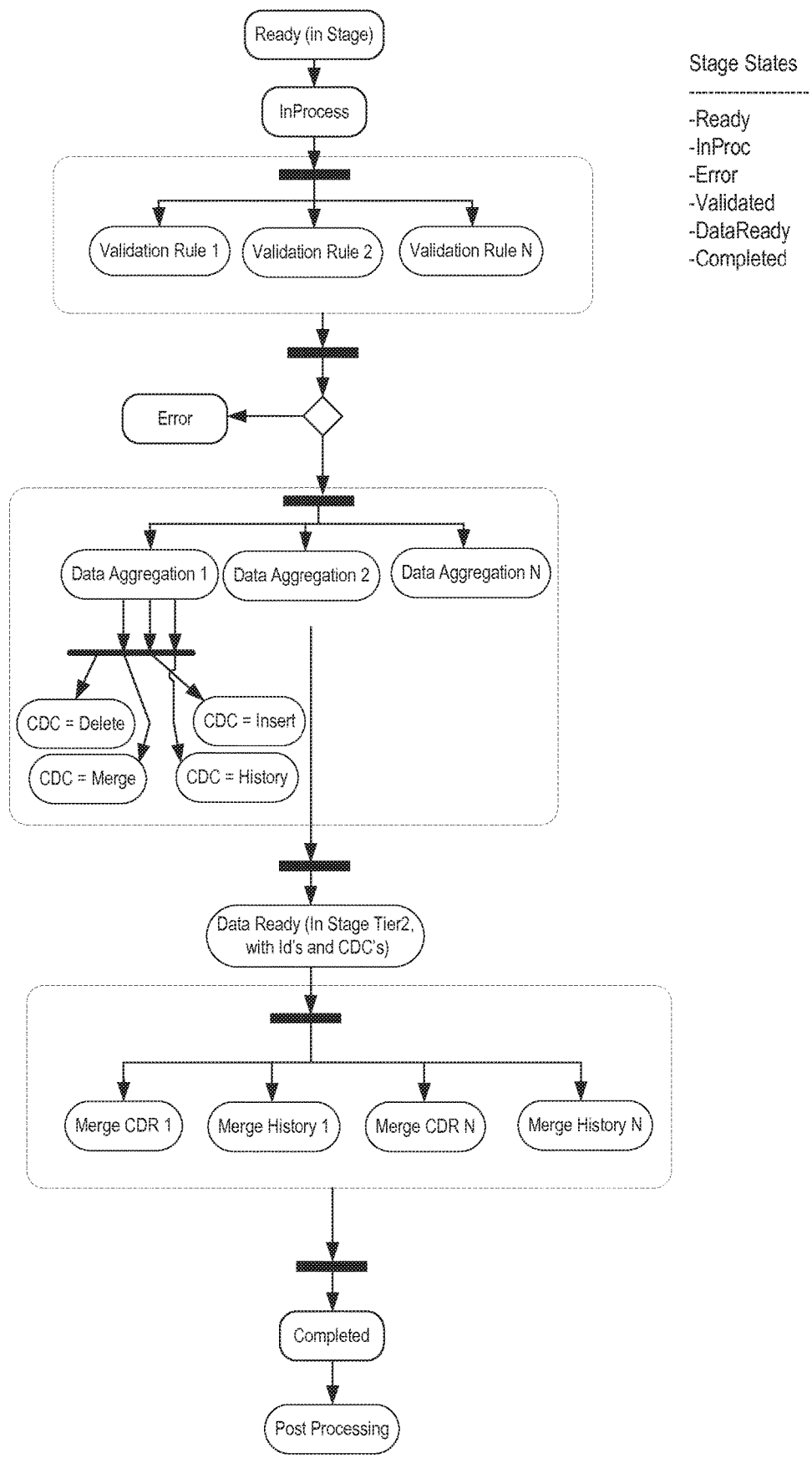
FIG. 13 illustrates an exemplary flowchart for a microbatch loading process.

In one or more preferred implementations, messages can be characterized by a state as they pass through a process for microbatch loading. FIG. 13 illustrates an exemplary flow chart for such a process.

A first of these states is a ready state, where a message is in the staging area and ready for processing. Once ready, processing of one or more messages begins, and a message transitions to an in process (or InProc) state. This processing preferably includes validation utilizing one or more validation rules, as illustrated in FIG. 13. If an error is discovered during this validation, an error state is triggered. If, however, no error occurs, then validated messages transition to a validated state, and move on to be aggregated. In one or more preferred implementations, during this aggregation process, change data capture information is identified. Following this aggregation, the data from the messages can be characterized as being at tier 2 staging in a data ready state for merging into a destination database. Thereafter, the data is systematically merged into the destination database as illustrated in FIG. 13, at which point the process is completed.

Figure 14:
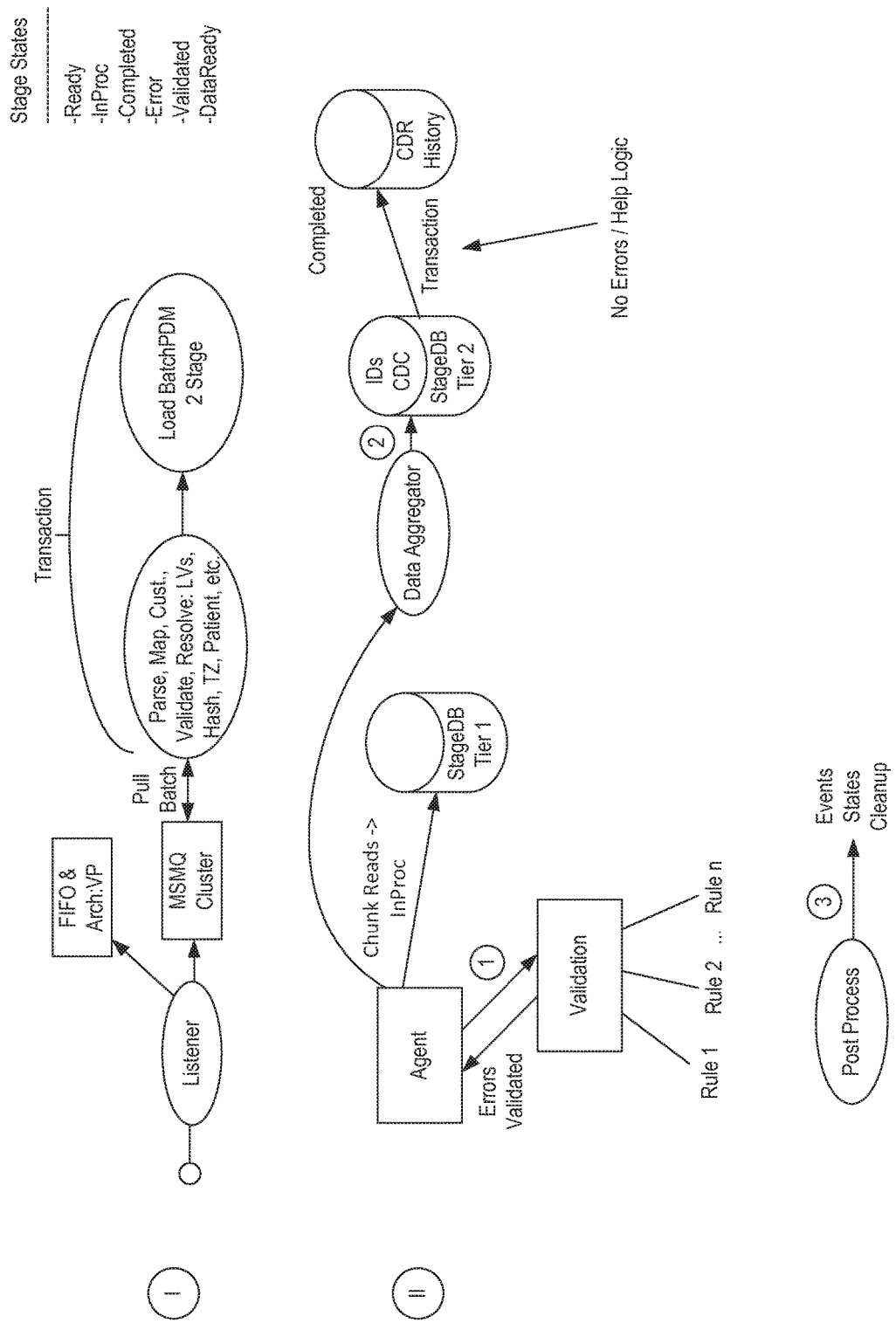
FIG. 14 schematically illustrates an exemplary implementation of a microbatch loading process.
Figure 15:
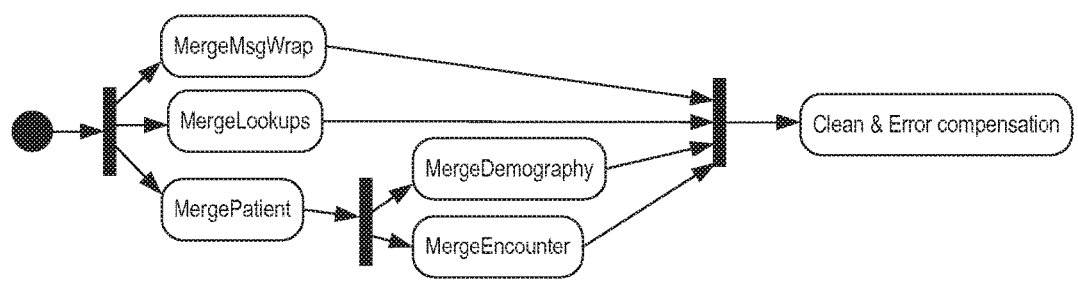
FIG. 15 illustrates an exemplary control flow for merging admission discharge transfer data.
Figure 16:
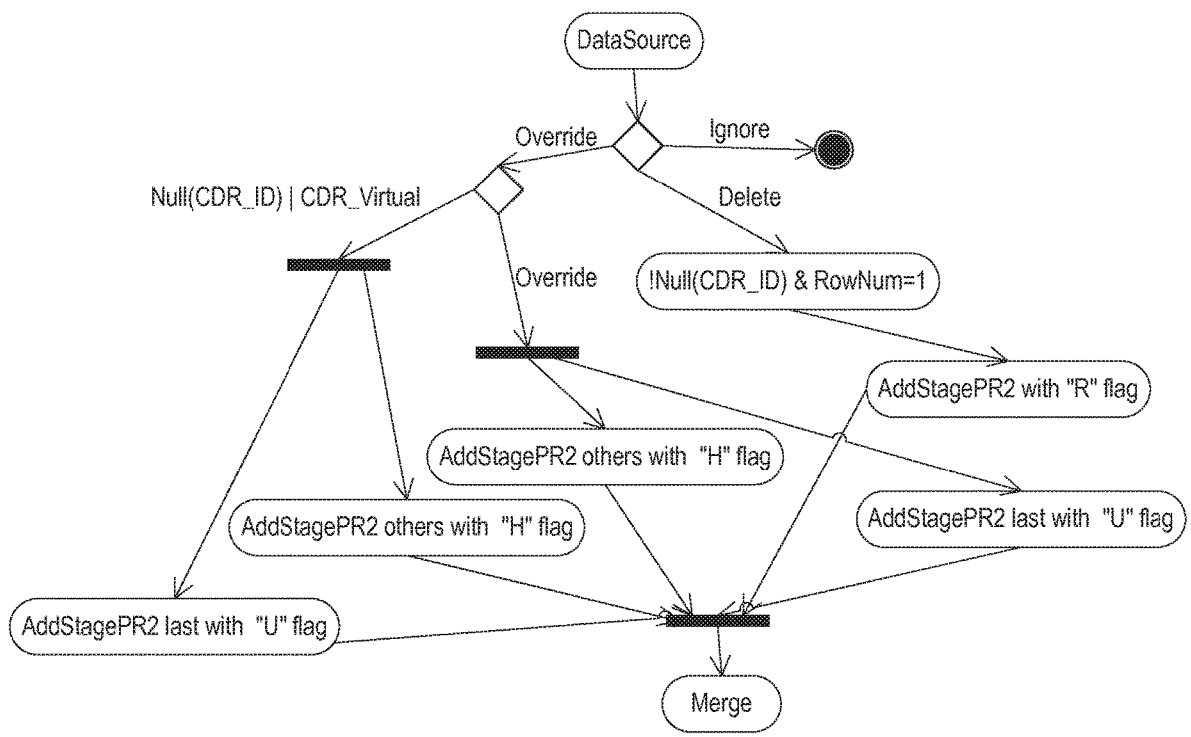
FIG. 16 drills down to a data aggregation flow related to "Patient" data from the control flow of FIG. 15.

FIG. 14 schematically illustrates an exemplary implementation of such a process. In a preferred implementation, a scheduler or agent takes a snapshot from all loaded data to stage (preferably using a table rather than SSB), and marks data for load. FIG. 15 illustrates an exemplary control flow for merging admission discharge transfer data, and FIG. 16 drills down to a data aggregation flow related to "Patient" data from the control flow.

In one or more preferred implementations, merging of data from a staging area to a CDR is accomplished by joining a stage data store to a CDR data store, with each act ordering by date of arrival. FIGS. 17-21 illustrate exemplary SQL code for processes in accordance with one or more preferred implementations.

In one or more preferred implementations, a stage data store comprises a new table with a CDCFlag column, and the stage data store is merged into CDR by the CDC flag, including satellite tables, with old tables being sent to history.

In one or more preferred implementations, the data aggregation process encapsulates all the LP logic, calculates identities (versus CDR), and set rows in stage with the concrete needed actions during the merge. Preferably, during the merge process, no logical errors are allowed, and environmental errors will fail the entire batch transaction. Preferably, all validation errors should be verified in the validation phase, and all types should already be converted in stage.

In one or more preferred implementations, messages will be fetched into batch processing by Common.Msg state and if there're no predecessor in FIFO. In one or more preferred implementations, using FIFO, a process in accordance with one or more preferred implementations can work in parallell to an old one, segmented by msgTypes.

In one or more preferred implementations, data validation, data aggregation, bulk Load and post processing are orchestrated by an application which will process whatever is possible. Preferably, chunk sizes (e.g. number or size of messages to be aggregated), degree of parallelism and polling interval will be configurable. In one or more preferred implementations, a sequential SQL job may be utilized.

In one or more preferred implementations, post processing includes logging, updating archive states, and cleanup.

In one or more preferred implementations, a transaction isolation level in the data aggregation and bulk load step verifies no phantom reads and non-repeatable reads. In one or more preferred implementations, the entire operation is atomic—single success or failure (rollback), assuming failures are all environmental.

Figure 22:
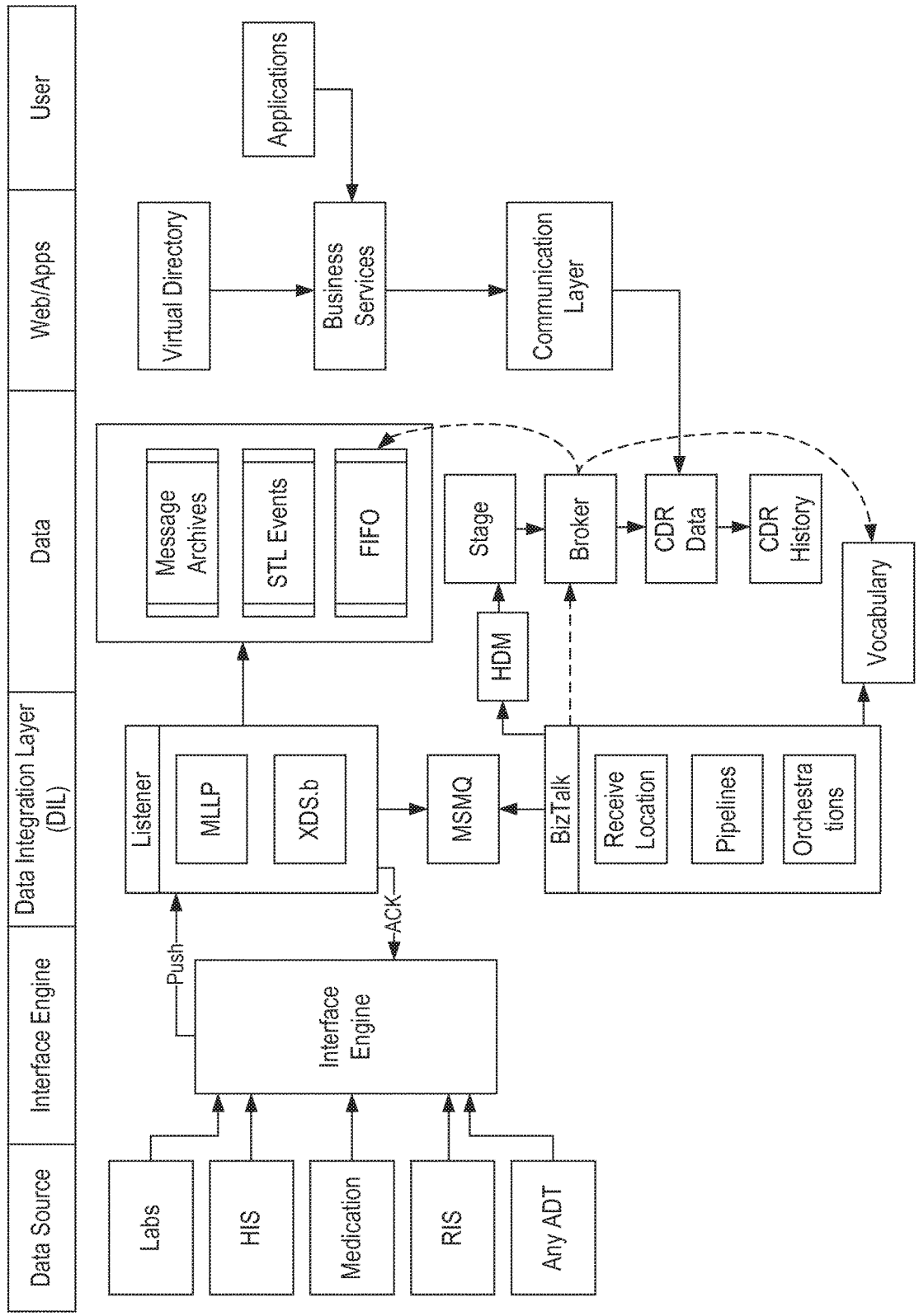
FIGS. 22-23 illustrate exemplary data flow for an exemplary implementation in accordance with one or more preferred embodiments.
Figure 23:
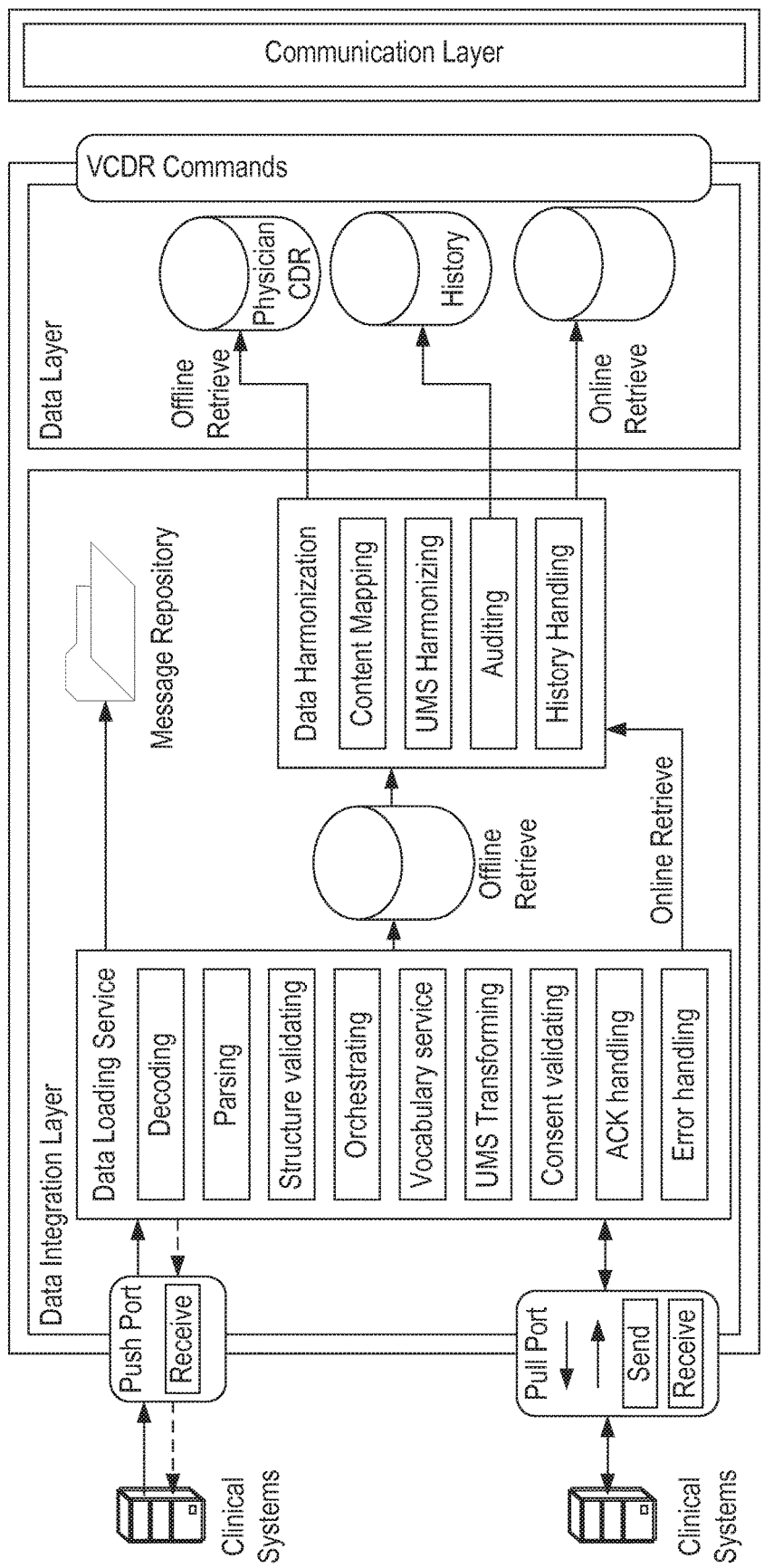

FIGS. 22-23 illustrate exemplary data flow for one or more exemplary implementations in accordance with one or more preferred embodiments. As illustrated in FIG. 22, a message is first received from a legacy system. Next, content of the message is verified according to protocol, the message is persisted, and a positive acknowledgement (or negative in the case of an error) is sent to the legacy system. The message is pulsed from the persistency store and parsed and transformed into a hierarchical object model. During the transformation, clinical and administrative codes and lookups are resolved. The message is normalized and persisted into a staging SQL DB.

The clinical data from the staging DB is loaded/merged into a Centralized Data Repository (CDR). The loading contains a specific loading policy for each act to be loaded. A loading policy defines the relation between the new message content and the content that exists in the CDR. For example, loading policies might include: Override, Additive, Reference-Additive, DeleteAll by parent act and override, differential Override, Override By specific keys and etc.

Preferably, during the load, a first-in-first-out loading order is maintained per patient as the legacy creates the messages in chronological order. Preferably, data which is overriden is sent to a history DB. Preferably, each message can later be replayed or undone.

One or more preferred implementations are believed to work in bulks. Preferably, one transaction will hold more data, providing greater scalability (e.g. more frequent bulks and larger bulks). Each bulk groups the data—avoiding unnecessary create, read, update, and delete (CRUD) operations. By working in bulks, this helps to overcome locks and transactions competition.

One or more preferred implementations leverage the power of a relational database management system (RDBMS) for set operations. In an exemplary implementation, clinical data from an incremental DB is merged into a centralized clinical repository with concrete loading policies.

In one or more preferred implementations, a pipeline working mode is utilized with preferably a non-blocking or semi-blocking bulk operation. In one or more preferred implementations, this results in parallelization of the process, better utilizing server resources and minimizing unused I/O or CPU resources at any given time.

One or more preferred implementations can be characterized with the following general principles:

Aggregate data in a staging area, merge into CDR an ordered, validated, calculated and manipulated sets instead of granular pieces of data.

Optimize aggregated sequential data.

First in, first out.

Load last piece—reduce the load from consumer capturing CDC's (Change Data Capture).

Ignore irrelevants.

Fail/Validate once.

Reduce CRUD operations and locks.

Leverage RDMBS—set based operations.

Do data manipulations, validations and calculations in batches.

Moving from an OLTP system to a semi ETL.

Ability to scale—regulate latency vs. rate. Bulk size and scheduling are adjustable, allowing for the increase of overall rate at the expense of latency.

A test scenario will now be described to illustrate potential advantages of utilizing processes in accordance with one or more preferred. In this test scenario, 216,000 messages were loaded simulating an hourly load of 60 messages per second. The messages contained 54,000 patients (25%) with override LP. FIFO was turned off, and patients sending order was shuffled to avoid deadlocks. Several applicative components were replaced with stubs to allow a high rate from DIL servers. On that server, that amount of messages took around five hours to load with very high CPU (10 SSB threads).

This scenario was repeated utilizing bulk scheduled loading. Working once every two minutes (bulks of 6200 messages). The messages were all processed several minutes after the last message was sent to the DIL.

Accumulating all 216,000 in stage, running the bulk loading in a progression mode, with bulks of 50,000 messages, took less than thirty minutes, and CPU wasn't very high. Each bulk ran in an isolated transaction.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A system comprising:
a staging computing device, the staging computing device comprising:
a processor; and
memory comprising instructions that, when executed by the processor, cause the processor to perform acts comprising:
receiving first transactional messages from a plurality of electronic health record applications (EHRs) executing on respective computing devices, the computing devices in communication with the staging computing device, wherein each of the first transactional messages comprises respective clinical data pertaining to a first patient, and wherein a portion of the clinical data in a first transactional message in the first transactional messages is duplicative of data in a second transactional message in the first transactional messages;
receiving second transactional messages, wherein each of the second transactional messages comprises respective clinical data pertaining to a second Patient
generating first aggregate transactional data representative of the clinical data pertaining to the first patient, wherein the first aggregate transactional data does not include the duplicative portion of the data from the first transactional messages;
generating second aggregate transactional data, the second aggregate transactional data representative of the clinical data pertaining to the second patient, wherein the second aggregate transactional data does not include duplicative data, wherein generating the first aggregate transactional data and generating the second aggregate transactional data are performed in parallel by the staging computing device;
transmitting the first aggregate transactional data to a server computing device that includes a data repository to cause the server computing device to merge the first aggregate transactional data into the data repository; and
transmitting the second aggregate transactional data to the server computing device to cause the server computing device to merge the second aggregate transactional data into the data repository.

2. The system of claim 1, further comprising the server computing device, wherein responsive to receiving the first aggregate transactional data, the server computing device merges the first aggregate transactional data into the data repository.

3. The system of claim 1,
sorting the first transactional messages and the second transactional messages into respective first and second patient queues, the first patient queue comprising transactional messages pertaining to the first patient, the second patient queue comprising transactional messages pertaining to the second patient.

4. The system of claim 1, wherein the first transactional messages are HL7 transactional messages.

5. The system of claim 1, wherein a number of transactional messages in the first transactional messages is configured by a user.

6. The system of claim 1, the acts further comprising validating the first transactional messages based upon a plurality of rules.

7. A method executed by a computing device in communication with one or more electronic health records applications (EHRs) and a server computing device that includes a data repository, the method comprising:

receiving transactional messages from the EHRs, the transactional messages comprising first transactional messages that include data pertaining to a first patient and second transactional messages that include data pertaining to a second patient;

sorting the first transactional messages and the second transactional messages into respective first and second patient queues;

generating a first aggregate transactional message based upon first messages in the first patient queue, the first aggregate transactional message representative of first data included in the first transactional message;

outputting the first aggregate transactional message to the server computing device;

generating a second aggregate transactional message based upon second messages in the second patient queue, the second aggregate transactional message representative of second data included in the second transactional message, wherein generating the first aggregate transactional message and generating the second aggregate transactional message are performed in parallel; and outputting the second aggregate transactional message to the server computing device.

8. The method of claim 7, wherein the transactional messages are HL7 transactional messages.

9. The method of claim 7, wherein at least a portion of a first message in the first transactional messages is duplicative of data in a second message in the first transactional messages, and wherein the first aggregate transactional message is not duplicative of the data in the second message.

10. The method of claim 7, further comprising validating the transactional messages based upon a plurality of rules.

11. The method of claim 10, wherein the validating the transactional messages is performed prior to outputting the first aggregate transactional message or outputting the second aggregate transactional message.

12. A computer-readable storage medium that stores computer-executable instructions that, when executed by a processor, cause the processor to perform acts comprising:

receiving a plurality of transactional messages from a plurality of electronic health record applications (EHRs) executing on respective computing devices, the transactional messages comprising first transactional messages that each comprise data pertaining to a first patient and second transactional messages that each comprise data pertaining to a second patient, wherein the first transactional messages include duplicative data, and wherein the second transactional messages include duplicative data;

sorting the first transactional messages into a first patient queue and the second transactional messages into a second patient queue;

generating a first aggregate transactional message based upon the first transactional messages in the first patient queue, the first aggregate transactional message representative of the data pertaining to the first patient, wherein the first aggregate transactional message does not include duplicative data;

generating a second aggregate transactional message based upon the second transactional messages in the second patient queue, the second aggregate transactional message representative of the data pertaining to the second patient, wherein the second aggregate transactional message does not include duplicative data;

outputting the first aggregate transactional message to a server computing device that includes a data repository, the first aggregate transactional message configured to cause the server computing device to merge the data pertaining to the first patient into the data repository; and outputting the second aggregate transactional message to the server computing device, the second aggregate transactional message configured to cause the server computing device to merge the data pertaining to the second patient into the data repository, wherein the instructions are configured to cause the processor to perform the generating of the first aggregate transactional message and the generating of the second aggregate transactional message in parallel.

13. The computer-readable storage medium of claim 12, wherein the transactional messages are HL7 transactional messages.

14. The computer-readable storage medium of claim 12, the acts further comprising:

validating the first transactional messages prior to generating the first aggregate transactional message; and validating the second transactional messages prior to generating the second aggregate transactional message.

15. The computer-readable storage medium of claim 12, wherein the data pertaining to the second patient and the data pertaining to the first patient are merged into a relational database in the data repository.

\* \* \* \* \*